US010632242B2

(12) United States Patent
Caluya et al.

(10) Patent No.: US 10,632,242 B2
(45) Date of Patent: Apr. 28, 2020

(54) RESOURCE-GENERATING DIALYSIS SYSTEM

(71) Applicant: Fresenius Medical Care Holdings, Inc., Waltham, MA (US)

(72) Inventors: Roger Caluya, Fremont, CA (US); Martin Joseph Crnkovich, Walnut Creek, CA (US); Bert D. Egley, Walnut Creek, CA (US); David Charles Griffith, Jr., Pittsburg, CA (US); Roland Levin, San Ramon, CA (US); Houssein Nasseri, Elk Grove, CA (US); Kulwinder S. Plahey, Martinez, CA (US); David Yuds, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 526 days.

(21) Appl. No.: 15/284,664

(22) Filed: Oct. 4, 2016

(65) Prior Publication Data
US 2017/0189597 A1    Jul. 6, 2017

Related U.S. Application Data

(60) Provisional application No. 62/273,724, filed on Dec. 31, 2015.

(51) Int. Cl.
*A61M 1/16* (2006.01)
*A61M 1/28* (2006.01)
(Continued)

(52) U.S. Cl.
CPC ............ *A61M 1/1656* (2013.01); *A61M 1/16* (2013.01); *A61M 1/166* (2014.02); *A61M 1/167* (2014.02);
(Continued)

(58) Field of Classification Search
CPC .. A61M 1/1656; A61M 1/166; A61M 1/1666; A61M 1/1668; A61M 1/167;
(Continued)

(56) References Cited

U.S. PATENT DOCUMENTS

| | | | |
|---|---|---|---|
| 2010/0022937 A1 | 1/2010 | Bedingfield et al. | |
| 2012/0043279 A1* | 2/2012 | Kelly ................. | A61M 1/1696 210/638 |

(Continued)

FOREIGN PATENT DOCUMENTS

| | | |
|---|---|---|
| EP | 2607323 A1 | 6/2013 |
| WO | WO2016132187 A1 | 8/2016 |

OTHER PUBLICATIONS

Notification of Transmittal of the International Search Report and the Written Opinion of the International Searching Authority from corresponding PCT Application No. PCT/US2016/055334, dated Jan. 12, 2017, 19 pages.

(Continued)

*Primary Examiner* — Philip R Wiest
(74) *Attorney, Agent, or Firm* — Fish & Richardson P.C.

(57) ABSTRACT

A dialysis system (e.g., a hemodialysis (HD) system) can be designed to operate in alternative environments, such as disaster relief settings or underdeveloped regions. The dialysis system can include a solar panel for generating electricity to power the dialysis machine and an atmospheric water generator for extracting water from ambient air. The extracted water can be used to generate dialysate and saline on-site. One or more of the components of the dialysis machine can be discrete components that are configured to facilitate fast shipping and simple on-site assembly (e.g., at a remote location). In some implementations, the discrete components may be configured to be attached to an existing dialysis system (e.g., a dialysis system designed for opera-
(Continued)

tion in a traditional environment) to permit the dialysis system to operate in an alternative environment.

13 Claims, 6 Drawing Sheets

(51) Int. Cl.
H02S 10/10 (2014.01)
H02S 40/38 (2014.01)
H02J 7/35 (2006.01)
B01D 5/00 (2006.01)
E03B 3/28 (2006.01)

(52) U.S. Cl.
CPC ........ *A61M 1/1666* (2014.02); *A61M 1/1668* (2014.02); *A61M 1/28* (2013.01); *B01D 5/0006* (2013.01); *H02J 7/355* (2013.01); *H02S 10/10* (2014.12); *H02S 40/38* (2014.12); A61M 2205/3606 (2013.01); A61M 2205/825 (2013.01); A61M 2205/8206 (2013.01); A61M 2205/8275 (2013.01); A61M 2205/8293 (2013.01); *E03B 3/28* (2013.01); *Y02A 20/109* (2018.01)

(58) Field of Classification Search
CPC .. A61M 1/16; A61M 1/28; A61M 2205/3606; A61M 2205/8206; A61M 2205/825; A61M 2205/8275; A61M 2205/8293; A61M 1/1629; A61M 1/3653; A61M 1/3672; A61M 1/3413; H02S 10/10; H02S 40/38
USPC ................................................ 604/4.01–6.16
See application file for complete search history.

(56) References Cited

U.S. PATENT DOCUMENTS

| 2013/0092361 | A1* | 4/2013 | Wrazel ...................... F28F 3/08 165/166 |
| 2013/0098814 | A1* | 4/2013 | Kelly ...................... C02F 1/008 210/85 |
| 2014/0284275 | A1 | 9/2014 | Boccato et al. |
| 2017/0173251 | A1* | 6/2017 | Doyle ................. A61M 1/1629 |

OTHER PUBLICATIONS

International Preliminary Report on Patentability in International Application No. PCT/US2016/055334, dated Jul. 3, 2018, 8 pages.

* cited by examiner

RESOURCE-GENERATING DIALYSIS SYSTEM

CROSS REFERENCE TO RELATED APPLICATION

This application claims priority under 35 USC §119(e) to U.S. Ser. No. 62/273,724 filed on Dec. 31, 2015. The contents of this priority application is hereby incorporated by reference in its entirety.

TECHNICAL FIELD

This invention relates to dialysis systems operable in areas of scarce resources, such as clean water and electricity.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis (HD)—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then typically discarded.

The dialysis solutions or dialysates used during hemodialysis typically contain sodium chloride and other electrolytes, such as calcium chloride or potassium chloride, a buffer substance, such as bicarbonate (e.g., sodium bicarbonate) or acetate (e.g., sodium acetate), and acid to establish a physiological pH, plus, optionally, a sugar such as glucose or dextrose.

Another type of dialysis treatment is peritoneal dialysis (PD) that utilizes the patient's own peritoneum, a membranous lining of the abdominal body cavity. With its good perfusion properties, the peritoneum is capable of acting as a natural semi-permeable membrane for transferring water and waste products to a type of dialysate solution known as PD solution introduced temporarily into the patient's abdominal cavity. An access port is implanted in the patient's abdomen and the PD solution is infused usually by a pump into the patient's abdomen through a patient line and left to dwell for a period of time. During the dwelling period, toxins are filtered from the patient's blood into the PD solution. The PD solution is then drained from the patient. This procedure is usually repeated multiple times for a complete treatment. PD machines, such as Automated PD (APD) machines or PD cyclers, are designed to facilitate or control the PD process so that it can be performed at home without clinical staff in attendance.

In many areas of the world and in emergency situations, reliable sources of clean water and electricity may not be available or practical to transport for dialysis patients. In such areas and situations, patients may not receive needed dialysis therapy. Accordingly, it would be desirable to provide a system that enables performance of dialysis treatments on a patient in an environment where resources such as clean water and electricity are scarce.

SUMMARY

In one aspect, a hemodialysis machine includes a blood pump configured to pump blood to and from a patient. The hemodialysis machine also includes a solar panel configured to receive light energy and generate electricity. The hemodialysis machine also includes an atmospheric water generator configured to be powered by the generated electricity and configured to extract water from ambient air. The extracted water is used to generate dialysate. The hemodialysis machine also includes a dialyzer configured to receive the blood and the dialysate, remove toxins from the blood, and provide filtered blood to the patient.

Implementations can include one or more of the following features.

In some implementations, the hemodialysis machine includes a sorbent device configured to remove toxins from spent dialysate flowing from the dialyzer.

In some implementations, the hemodialysis machine includes a battery configured to store a charge derived from the generated electricity.

In some implementations, the hemodialysis machine includes a water heater configured to heat the extracted water.

In some implementations, the water heater includes a container for storing heated water.

In some implementations, the water heater includes a second solar panel configured to receive light energy that is used to heat the extracted water.

In some implementations, the blood pump includes a mechanical component that is configured to be manually operated.

In some implementations, the mechanical component includes one or both of a hand pump and a foot pump.

In some implementations, the mechanical component is configured to generate electricity in response to manual operation of the blood pump.

In some implementations, the hemodialysis machine includes a battery configured to store a charge derived from the electricity generated by one or both of the mechanical component and the solar panel.

In some implementations, the blood pump includes one or more valves configured to control a flow rate of the blood pumped to and from the patient.

In some implementations, the hemodialysis machine includes a forward osmosis container. The forward osmosis container includes a first compartment configured to store a salt concentrate, a second compartment configured to receive the extracted water, and a membrane that separates the first compartment from the second compartments. The membrane is configured to allow the extracted water to mix with the salt concentrate to produce a saline solution.

In another aspect, a hemodialysis machine includes a generator configured to generate electricity in response to mechanical motions performed by an operator of the hemodialysis machine. The hemodialysis machine also includes a blood pump configured to pump blood to and from a patient. The hemodialysis machine also includes a processor in communication with the blood pump. The processor is powered by the generated electricity and is configured to control a dialysis treatment administered to the patient. The hemodialysis machine also includes an atmospheric water generator that is powered by the generated electricity and configured to extract water from ambient air. The extracted water is used to generate dialysate. The hemodialysis machine also includes a dialyzer configured to receive the blood and the dialysate, remove toxins from the blood, and provide filtered blood to the patient.

Implementations can include one or more of the following features.

In some implementations, the generator includes one or both of a hand pump and a foot pump.

In some implementations, the processor is configured to control a flow rate of the blood pumped to and from the patient.

In some implementations, the hemodialysis machine includes a battery configured to store a charge derived from the generated electricity.

In some implementations, the hemodialysis machine includes a solar panel configured to receive light energy and generate electricity.

In some implementations, the hemodialysis machine includes a battery configured to store a charge derived from the electricity generated by one or both of the generator and the solar panel.

In some implementations, the hemodialysis machine includes a water heater configured to heat the extracted water.

In some implementations, the hemodialysis machine includes a sorbent device configured to remove toxins from spent dialysate flowing from the dialyzer.

In some implementations, the hemodialysis machine includes a forward osmosis container. The forward osmosis container includes a first compartment configured to store a salt concentrate, a second compartment configured to receive the extracted water, and a membrane that separates the first compartment from the second compartments. The membrane is configured to allow the extracted water to mix with the salt concentrate to produce a saline solution.

In another aspect, a peritoneal dialysis (PD) machine includes a solar panel configured to receive light energy and generate electricity. The PD machine also includes an atmospheric water generator configured to be powered by the generated electricity and configured to extract water from ambient air. The extracted water is used to generate a PD solution. The PD machine also includes a pump configured to pump the PD solution to and from an abdominal cavity of a patient. Toxins are removed from blood of the patient as the PD solution resides in the abdominal cavity.

Implementations can include one or more of the following advantages.

In some implementations, the systems and methods described herein can allow a dialysis system to operate in alternative environments, such as environments where clean water and electricity are scarce, dialysate is unavailable, or appropriate dialysate storage conditions do not exist. Such environments can include disaster relief settings, emergency response settings, underdeveloped regions, and/or developing countries, to name a few.

In some implementations, the dialysis system can produce resources necessary for operating the dialysis machine and administering a dialysis treatment. For example, the solar panel can be used to generate electricity using light energy from the sun, the atmospheric water generator can be used to extract water from ambient air. The extracted water can be used to generate dialysate and/or saline on-site, obviating the need for prolonged storage of such substances which may otherwise be difficult, impracticable, or impossible based on the particular environmental conditions.

In some implementations, one or more of the components of the dialysis machine can be discrete components that can be transported to a remote location and attached to an existing dialysis machine (e.g., a dialysis machine designed for operation in a more traditional environment), thereby permitting the dialysis machine to operate in an alternative environment.

The details of one or more implementations of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Dialysis machines (e.g., hemodialysis (HD) machines or peritoneal dialysis (PD) machines) are typically designed to operate in medical facilities such as hospitals and dialysis clinics, to name a couple. Some dialysis machines are also designed for use in a patient's home. Such environments offer the resources necessary for proper administration of dialysis treatment. For example, clean water and electricity are readily available for use by the dialysis machine; dialysate is readily available in medical facilities, and dialysate can be provided to patients for home use and storage under appropriate storage conditions.

A dialysis system can be designed to operate in alternative environments, such as environments where clean water and electricity are scarce, dialysate is unavailable, or appropriate dialysate storage conditions do not exist. Examples of such environments can include disaster relief settings or underdeveloped regions (e.g., developing countries). The dialysis system can include a solar panel for generating electricity to power the dialysis machine and an atmospheric water generator for extracting water from ambient air. The extracted water can be used to generate dialysate and saline on-site.

Some of the components of the dialysis machine can be discrete components that are configured to facilitate fast transport (e.g., fast shipping) and simple assembly. For example, the discrete components can be transported to a remote location and assembled on-site. The discrete components may be configured to be attached to an existing dialysis system (e.g., a dialysis system designed for operation in a traditional environment) to permit the dialysis system to operate in an alternative environment.

Figure 1:
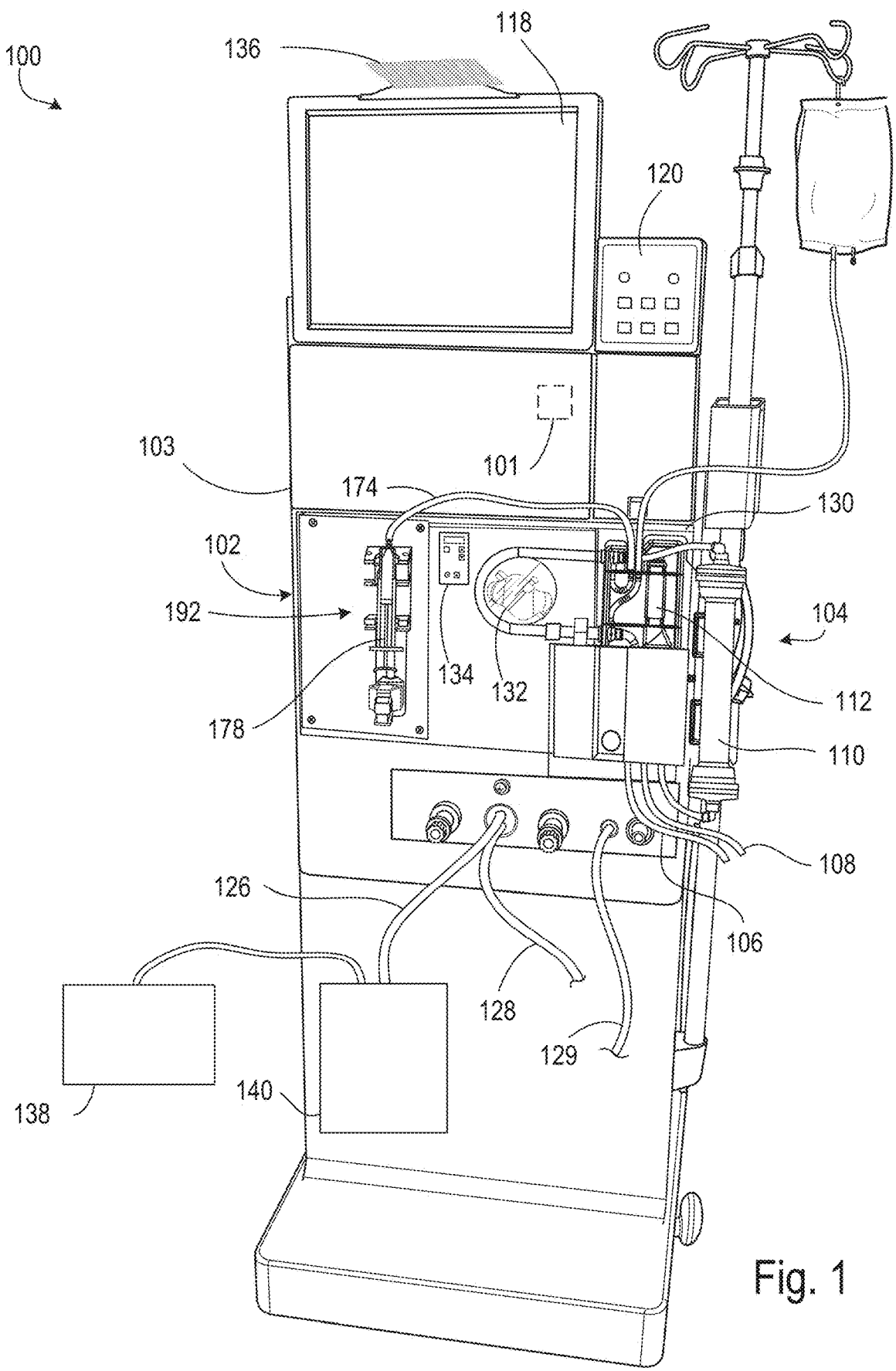
FIG. 1 is a front perspective view of a hemodialysis system that includes a solar panel and an atmospheric water generator.

FIG. 1 shows a dialysis system, such as a hemodialysis system 100, configured for operating in an alternative environment. Although the system described herein is largely discussed in connection with hemodialysis systems by way of example, it is explicitly noted that the system described herein may be used in connection with other types of medical devices and treatments, including peritoneal dialysis (PD) systems. The hemodialysis system 100 includes a hemodialysis machine 102, a solar panel 136 for generating electricity to power the hemodialysis machine 102, and an atmospheric water generator 138 for extracting water from ambient air to be used for generating dialysate and/or saline on-site.

The hemodialysis machine 102 is connected to a disposable blood component set 104 that partially forms a blood circuit. During hemodialysis treatment, an operator connects arterial and venous patient lines 106, 108 of the blood component set 104 to a patient. The blood component set 104 includes an air release device 112, which contains a self-sealing vent assembly that allows air but does not allow liquid to pass. As a result, if blood passing through the blood circuit during treatment contains air, the air release device 112 will vent the air to atmosphere.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment that is sized and shaped to receive the blood component set 104. In the closed position, the door presses certain blood components of the blood component set 104 against corresponding instruments exposed on the front face of the module 130.

The operator uses a blood pump module 134 to operate the blood pump 132. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber. The blood pump module 134 may also include a level detector that includes one or more sensors for determining the level of the fluid in the arterial drip chamber.

The hemodialysis machine 102 further includes a dialysate circuit formed by the dialyzer 110, various other dialysate components, and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

The atmospheric water generator 138 is configured to extract water from humidity in ambient air and provide the extracted water to one or more portions of the hemodialysis machine 102, as described in more detail below. In particular, the atmospheric water generator 138 provides water to a mixing chamber 140, where the water mixes with a concentrate (e.g., a solid concentrate), such as a powdered sodium bicarbonate concentrate, to produce a mixed sodium bicarbonate solution.

In general, during operation the mixing chamber 140 includes a layer of sodium bicarbonate solution over a layer of powdered sodium bicarbonate concentrate because the powdered sodium bicarbonate is denser than the solution and rests on the bottom of the mixing chamber. As water from the atmospheric water generator 138 is added to the mixing chamber 140, the water falls into the layer of solution causing agitation in the portion of the solution directly adjacent the layer of undissolved sodium bicarbonate powder and thereby causing the sodium bicarbonate powder to become mixed with the solution. This mixing action assists in the dissolution of the sodium bicarbonate powder into the solution, and thus helps to ensure that the solution becomes saturated. The sodium bicarbonate solution can be used as a component of the dialysate. In some implementations, one or more other substances may be combined with the sodium bicarbonate solution. For example, electrolytes such as sodium chloride, calcium chloride, or potassium chloride, acetate, and/or acids may be added to the bicarbonate solution (e.g., via a supply line 128) to create the dialysate.

The mixing chamber 140 is connected to the hemodialysis machine 102 via a dialysate supply line 126. A drain line and an ultrafiltration line 129 also extend from the hemodialysis machine 102. In some implementations, the drain line is located at the back of the hemodialysis machine 102 and therefore is not visible in FIG. 1. The dialysate supply line 126, the drain line, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the mixing chamber 140 to the portion of the dialysate circuit located inside the hemodialysis machine 102. As noted above, the fresh dialysate is circulated through various dialysate lines and dialysate components, including the dialyzer 110, that form the dialysate circuit. As will be described below, as the dialysate passes through the dialyzer 110, it collects toxins from the patient's blood. The resulting spent dialysate is carried from the dialysate circuit to a drain via the drain line. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain. In some implementations, if a sorbent device is used, the spent dialysate is recirculated through a sorbent filter, as described in more detail below.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a user interface with input devices such as a touch screen 118 and a control panel 120. The touch screen 118 and the control panel 120 allow the operator to input various different treatment parameters to the hemodialysis machine 102 and to otherwise control the hemodialysis machine 102. The touch screen 118 displays information to the operator of the hemodialysis system 100.

The hemodialysis machine 102 also includes a control unit 101 (e.g., a processor) configured to receive signals from and transmit signals to the touch screen 118, the control panel 120, and the blood pump module 134. The control unit 101 can control the operating parameters of the hemodialysis machine 102, for example, based at least in part on the signals received from the touch screen 118, the control panel 120, and the blood pump module 134, so as to control the dialysis treatment administered to the patient. For example, the control unit 101 is configured to control the flow rate of the blood pumped to and from the patient, e.g., based on signals received from the blood pump module 134. In some implementations, the blood pump module 134 may include its own control unit (e.g., processor) that is configured to control operating parameters associated with blood flow rate.

Figure 2:
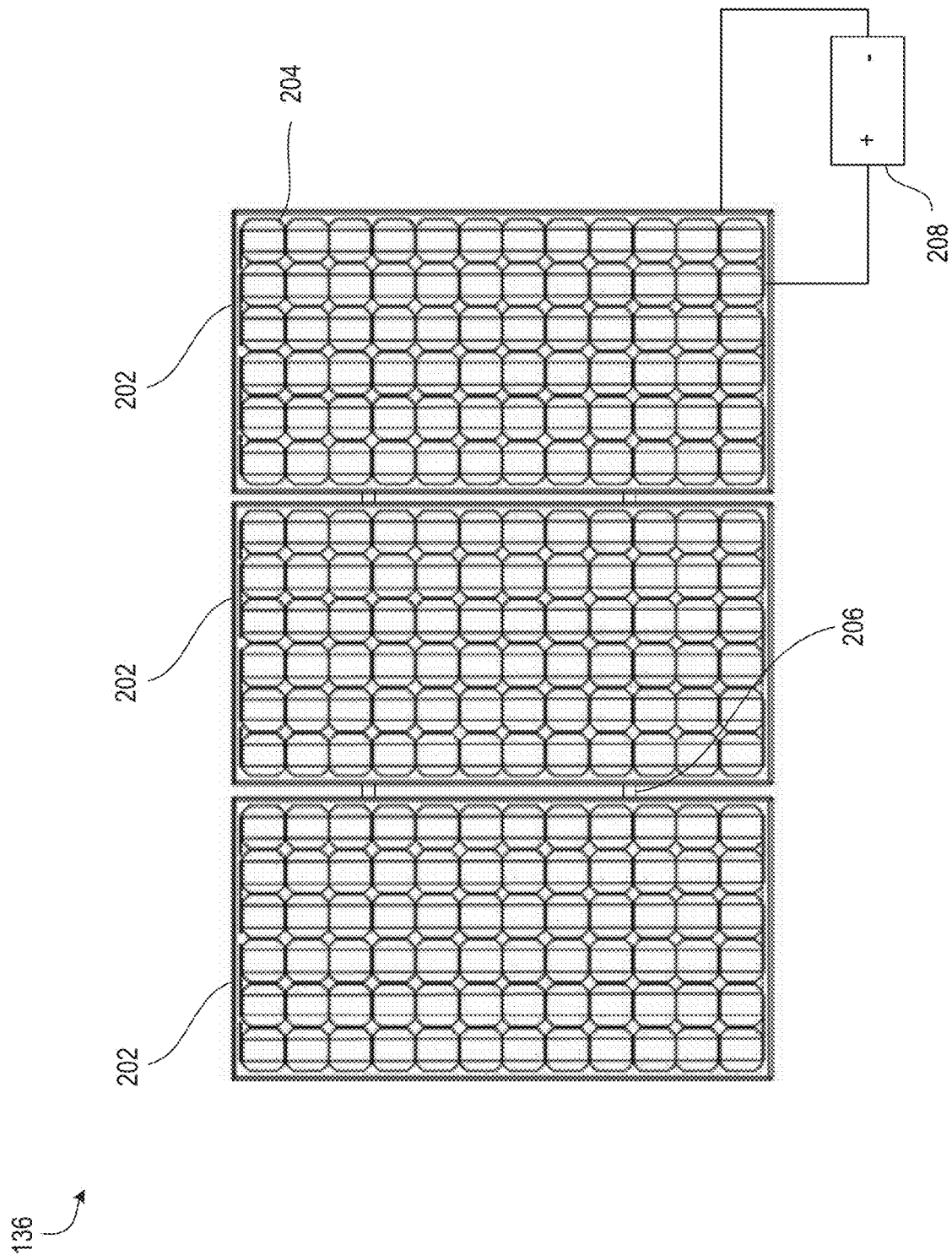
FIG. 2 shows an example of the solar panel of FIG. 1.

FIG. 2 shows an example of the solar panel 136 of FIG. 1. The solar panel 136 is configured to generate electricity for powering components of the hemodialysis machine 102. The solar panel 136 includes electrically-connected solar modules 202 that each includes a plurality of solar cells 204. The solar modules 202 are attached to each other by connectors 206.

The solar cells 204 receive (e.g., from the sun) light energy in the form of photons, and use the received light energy to generate electricity. Electricity is generated through the photovoltaic effect, which is a physical and chemical phenomenon that causes voltage and current to be created in the solar cells 204. The characteristics of the generated electricity is based in part on the materials used for the solar cells 204. In some implementations, the solar cells 204 can include one or more of wafer-based crystalline silicon, thin-film cadmium telluride, thin-film silicon, and compound semiconductors such as gallium arsenide, to name a few.

The connectors 206 may allow the solar modules 202 to pivot such that the solar modules 202 can be oriented toward the sun. The position of the sun relative to the horizon is dependent on the geographic location of the hemodialysis machine 102, and the position of the sun relative to the horizon changes as the day progresses. The solar modules 202 can be positioned and oriented based on the time of day and the geographic location of the hemodialysis machine 102 such that the solar modules 202 point directly at the sun, thereby maximizing the amount of electricity that can be generated.

The connectors 206 may be hinges that allow the solar modules 202 to pivot relative to each other. In some implementations, the connectors 206 may allow the solar modules 202 to fold on top of each other to facilitate storage and shipment.

In this example, the solar panel 136 is configured to electrically connect to a battery 208. The battery 208 may be a rechargeable battery that is configured to store a charge that is derived from the electricity generated by the solar panel 136. The battery 208 can be electrically connected to the hemodialysis machine 102 to provide power to the hemodialysis machine 102 and its associated components. In this way, the hemodialysis machine 102 can be powered even when solar generation of electricity is not possible or when conditions for solar generation of electricity are suboptimal (e.g., at night, when the sun is blocked by clouds, when the solar panel 136 is not in line-of-sight with the sun, etc.). In some implementations, the battery 208 may be provided in the hemodialysis machine 102 (e.g., within the housing 103 of the hemodialysis machine 102).

Figure 3:
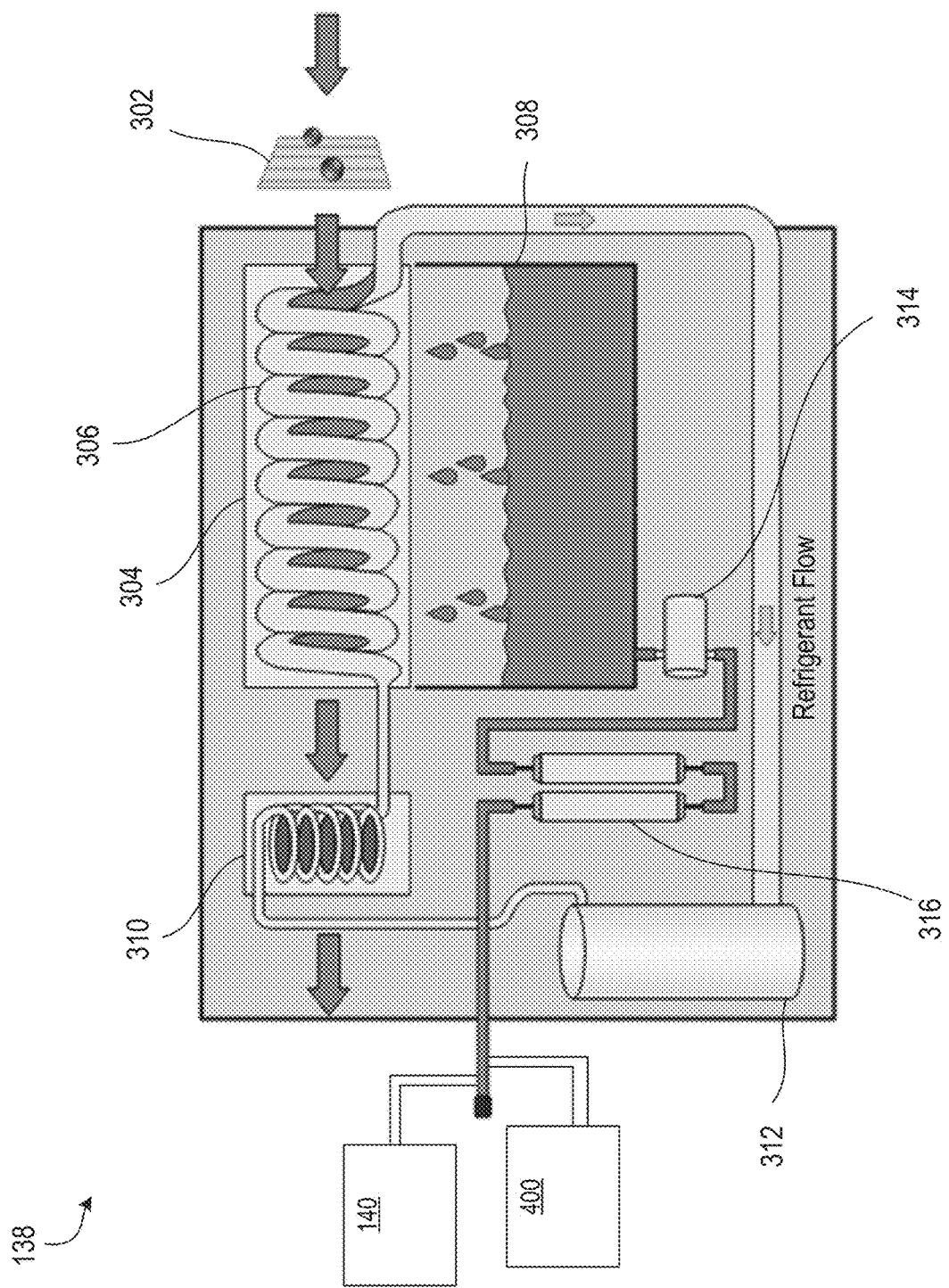
FIG. 3 shows a schematic view of the atmospheric water generator of FIG. 1.

As described above, the hemodialysis machine 102 is configured to generate water that can be used for operation in environments where clean water is scarce. FIG. 3 shows a schematic view of the atmospheric water generator 138 of FIG. 1. The atmospheric water generator 108 is configured to extract water from humidity in ambient air.

Air having at least some degree of humidity (i.e., air that includes at least some water vapor) enters the atmospheric water generator 138 through an air filter 302. The air filter 302 removes unwanted dirt or particles from the air that may otherwise contaminate the extracted water. The filtered air is passed to an evaporator 304. The evaporator 304 includes a coil 306 that is cooled by refrigerant that flows through the coil 306. As the air passes over the cooled coil 306, the temperature of the air lowers to its dew point, thereby causing the humidity in the air to condense into water. The extracted water is passed into a container 308 for storing the water.

The refrigerant is circulated through the coil 306 and a condenser 310 by a compressor 312. The refrigerant arrives at the compressor 312 as a cool, low pressure gas. The compressor 312 compresses the refrigerant into a hot, high pressure gas that flows into the condenser 310. The condenser 310 acts to dissipate some of the heat from the refrigerant. Thus, when the refrigerant exits the condenser 310, the refrigerant has a relatively cool temperature. The liquid refrigerant enters the coil 306 of the evaporator 304 and cools the coil 306 such that the air passing over the coil 306 (e.g., the humid air entering the atmospheric water generator 108 through the air filter 302) is cooled below its dew point. The humidity in the air is condensed into water and stored in the container 308. The refrigerant then flows back to the compressor 312 to be recirculated in a similar manner.

The atmospheric water generator 138 may be configured as an online water generation source. That is, the atmospheric water generator 138 may extract water from ambient air and use the extracted water to generate dialysate and/or saline immediately or substantially immediately after being extracted. In some implementations, the atmospheric water generator 138 is primarily used to store extracted water (e.g., in the container 308) for later use. For example, if the atmospheric water generator 138 is incapable of extracting water at a sufficient rate to satisfy the needs of the hemodialysis system 100, the atmospheric water generator 138 may be operated prior to administration of a dialysis treatment to provide enough time to extract a sufficient quantity of water.

The atmospheric water generator 138 also includes a pump 314 for providing the extracted water to other portions of the hemodialysis machine 102. The extracted water may undergo one or more additional filtering steps, including running the extracted water through an ultrapure filter. The pump 314 is then configured to pump the water to the mixing chamber 140 where the water is mixed with a concentrate and electrolytes to generate the dialysate. In some implementations, the generated dialysate may be stored in a dialysate reservoir before it is supplied to the dialysate circuit. The dialysate reservoir may be configured to store approximately six liters of dialysate. In some implementations, the extracted water may initially be provided to the dialysate reservoir before it is pumped to the mixing chamber 140. The water may then be mixed with concentrate and electrolytes to generate the dialysate, and the generated dialysate may be pumped back to the dialysate reservoir. In some implementations, the extracted water continuously circulates through the dialysate reservoir, the mixing chamber 140, and back to the dialysate reservoir. In this way, a constant supply of dialysate generated using freshly extracted water may be available.

The generated dialysate may meet an International Organization for Standardization (ISO) standard, an American National Standards Institute (ANSI) standard, and/or an Association for the Advancement of Medical Instrumentation (AAMI) standard such as ISO/ANSI/AAMI 11663: 2014 covering quality of dialysis fluid for hemodialysis and related therapies or ISO/ANSI/AAMI 23500:2014 covering guidance for the preparation and quality management of fluids for hemodialysis and related therapies. The concentrates used in generation of the dialysate may meet an ISO/ANSI/AAMI standard such as ISO/ANSI/AAMI 13958:2014 covering concentrates for hemodialysis and related therapies.

The pump 314 of the atmospheric water generator 138 may also be configured to pump the water to a forward osmosis container 400 of FIG. 4 to be used for generating a saline solution, as described in more detail below. The atmospheric water generator 138 can include one or more 316 that are configured to remove dirt, particles, toxins, etc. from the water before the water is provided to various portions of the hemodialysis machine 102. In this way, the water can be properly conditioned prior to being used to generate dialysate and/or saline and prior to being introduced to the patient.

In some implementations, the extracted water is heated before it is provided to other portions of the hemodialysis machine 102. In some implementations, a water heater including one or more heating elements may be incorporated into the atmospheric water generator 138. For example, the water heater may be incorporated into the container 308 that is used to store the extracted water. In some implementations, the container 308 and the incorporated water heater can also serve to pressurize and/or degas the water so as to produce ISO quality water that is used to generate the dialysate and/or the saline, as described in more detail below. In some examples, the water may meet an ISO/ANSI/ AAMI standard such as ISO/ANSI/AAMI 13959:2014 covering water for hemodialysis and related therapies, and the equipment used to generate, heat, and/or degas the water (e.g., the atmospheric water generator 138, the water heater, and/or the mixing chamber 104) may meet an ISO/ANSI/ AAMI standard such as ISO/ANSI/AAMI 26722:2014 covering water treatment equipment for hemodialysis applications and related therapies.

The water can be heated upon being extracted such that the water is at an appropriate temperature when it is needed, thereby reducing or eliminating delay. The water heater may include a coil made of an alloy, such as a nickel and/or chromium alloy. In some implementations, the water heater includes sheathed heater elements. The water heater may be powered by the electricity generated by the solar panel 136 (e.g., directly or via the battery 208 of FIG. 2). In some implementations, the water heater has its own energy source. For example, the water heater may include its own solar panel (e.g., other than the solar panel 136 shown in FIG. 1) for generating electricity that is used to power the heating elements.

During operation of the hemodialysis system 100, a saline solution may be introduced to the patient via an intravenous (IV) line. The saline may be used for a variety of reasons, including priming and flushing bloodlines, providing a pathway for the delivery of pharmaceuticals, etc. For example, one or more pharmaceutical substances may be mixed into the saline before the solution is provided to the patient via the IV line. Saline is sometimes provided in prepackaged bags. In some examples, saline can be generated on demand by mixing water with a salt concentrate.

In some implementations, the hemodialysis system 100 includes a sorbent device (e.g., a sorbent cartridge/filter) that is configured to recycle spent dialysate so that the spent dialysate can be reused for hemodialysis treatment. As described above with reference to FIG. 1, as the dialysate passes through the dialyzer 110, the dialysate collects toxins from the patient's blood. The resulting spent dialysate can be carried from the dialysate circuit to a drain via the drain line, and new dialysate can be used for subsequent treatment. However, in some implementations, the spent dialysate can be provided to the sorbent device, which can remove the toxins (e.g., such as urea) from the spent dialysate. The recycled dialysate can then be cycled back through the dialysate circuit and reused to cleanse the patient's blood.

In some implementations, one or more undesired substances (e.g., uric acid, middle molecules, oxidants, etc.) may be stripped from the dialysate as the dialysate passes through the sorbent device. In some implementations, one or more desired substances (e.g., magnesium, calcium, potassium, sodium, etc.) may be added to the dialysate exiting the sorbent device (e.g., prior to the dialysate being reintroduced into the dialysate circuit). In some implementations, water (e.g., water extracted by the atmospheric water generator 138) can be introduced into the recycled dialysate for dilution purposes if the sodium concentration of the recycled dialysate is too high.

In some implementations, in addition to the sorbent device being used to cleanse the spent dialysate, the sorbent device may be used to assist the mixing chamber 140 in generating the dialysate. In some examples, the water generated by the atmospheric water generator 138 passes through the sorbent device for filtering prior to being provided to the mixing chamber 140. In this way, the extracted water can be further filtered and purified prior to being used to generate dialysate.

In some implementations, the sorbent device can be used instead of the mixing chamber 140 to produce the dialysate. For example, extracted water provided by the atmospheric water generator 138 may be mixed with electrolytes and filtered through the sorbent device to generate dialysate that is delivered to the dialysate circuit via the dialysate supply line 126. After the dialysate passes through the dialyzer 110 and collects toxins from the patient's blood, the spent dialysate may be cycled back through the sorbent device where it can be recycled for reuse.

Figure 4:
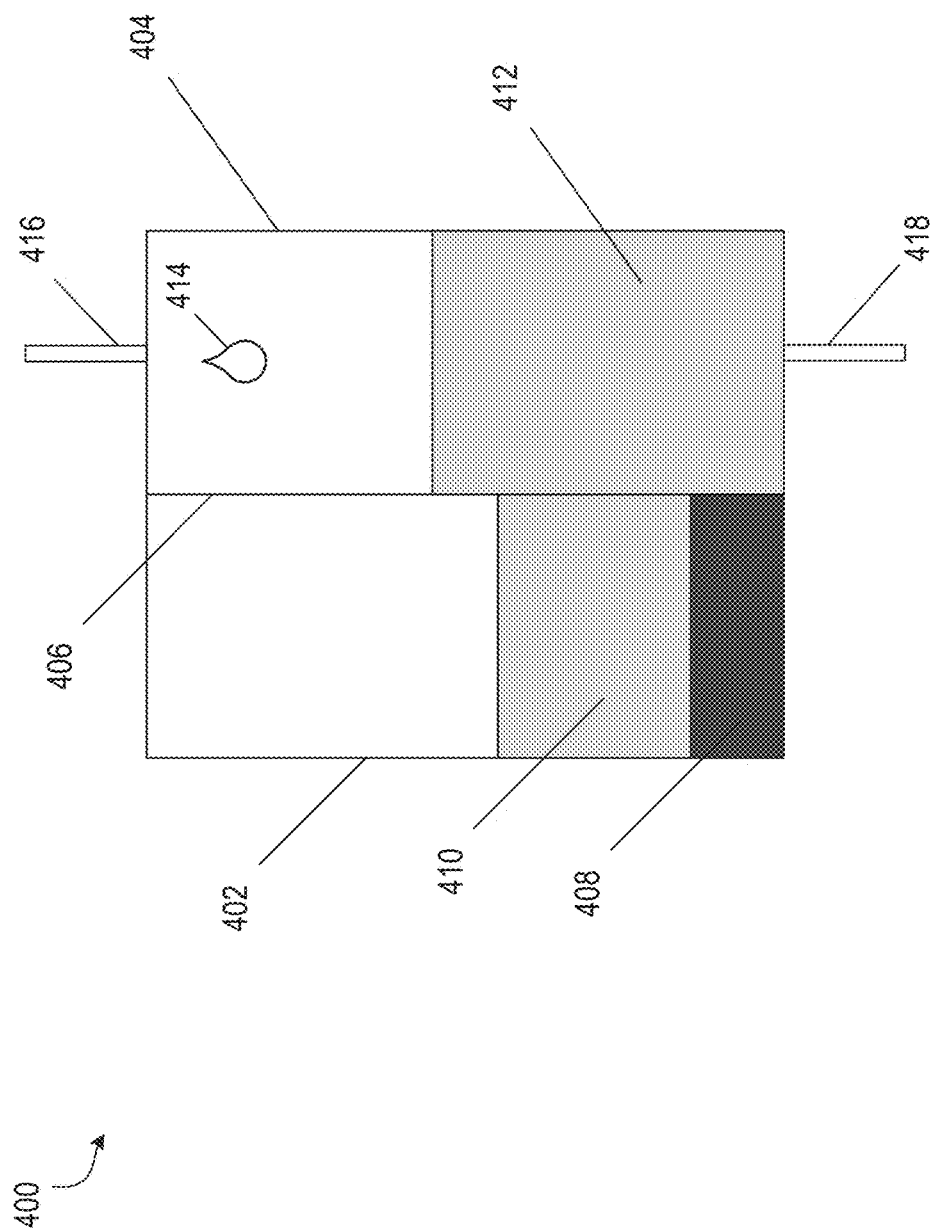
FIG. 4 shows an example of a forward osmosis container.

FIG. 4 shows an example of a forward osmosis container 400 that is configured to allow water to mix with a salt concentrate to produce a saline solution. The forward osmosis container 400 may be in the form of a bag (e.g., a disposable bag). The forward osmosis container 400 includes a first compartment 402, a second compartment 404, and a membrane such as a semi-permeable membrane 406 that separates the first compartment from the second compartment. In some implementations, the compartments 402, 404 may be reusable and the semi-permeable membrane 406 may be disposable. The disposable semi-permeable membrane 406 may be replaced with a new semi-permeable membrane 406 when its end-of-life has been reached.

The first compartment 402 is configured to store a salt concentrate 408, such as sodium chloride. Water 414 (e.g., water generated by the atmospheric water generator 138 of FIGS. 1 and 3) enters the second compartment 404 of the forward osmosis container 400 via an inlet 416. As the water 414 is introduced into the second compartment 404, the semi-permeable membrane 406 allows the water 414 to pass into the first compartment 402 and mix with the salt concentrate 408. The semi-permeable membrane 406 does not allow the salt concentrate 408 to pass into the second compartment 404. The mixing of the water 414 and the salt concentrate 408 results in a first salt concentrate solution 410 (e.g., a high-concentration salt concentrate solution) accumulating in the first compartment 402.

As water 414 continues to be introduced into the second compartment 404, a second salt concentrate solution 412 (e.g., a relatively lower-concentration salt concentrate solution) accumulates in the second compartment 404. In particular, some of the first salt concentrate solution 410 passes into the second compartment 404 and mixes with the introduced water 414 to form the second salt concentrate solution 412. The degree of transfer and the resulting concentration of the second salt concentrate solution 412 that accumulates in the second compartment 404 is based on an osmotic pressure gradient between the first solution 410 and the second solution 412. The concentration of the second salt concentrate solution 412 may depend on characteristics of the salt concentrate 408, the amount of salt concentrate 408 provided in the first compartment 402, and characteristics of the semi-permeable membrane 406 such as the hydraulic permeability of the membrane 406, among others. The second solution 412 having an appropriate salt concentration (e.g., a salt concentration commensurate with saline) may then be provided to the patient via an outlet 418.

In some implementations, the forward osmosis container 400 may be a disposable bag that is filled with the salt concentrate 408 at the time of manufacturing. The disposable bag may be affixed to an IV pole (not shown). The output of the atmospheric water generator 138 can be attached to the inlet 416 and the outlet 418 can be introduced to the patient (e.g., via an IV line). In some implementations, the forward osmosis container 400 includes one or more sensors for monitoring pressure or flow rate within the compartments 402, 404 of the forward osmosis container 400. Measurements from pressure or flow rate sensors may be used to determine or predict a salt concentration of the first or second salt concentrate solutions 410, 412. In some implementations, one or more conductivity sensors can be used to determine the conductivity of the first or second salt concentrate solutions 410, 412. Such conductivity measurements can be used to ascertain the salt concentration of the first and second salt concentration solutions 410, 412.

One or more of the components of the hemodialysis system 100 may be discrete components that can be incorporated into the hemodialysis system 100 separately (e.g., after initial manufacturing of the base hemodialysis system 100). In some implementations, an existing hemodialysis system may be fitted with the solar panel 136, an atmospheric water generator 138, and/or a mixing chamber 140 for adapting the hemodialysis system into a system that can operate in extreme conditions.

In some examples, a hemodialysis system may be configured to be operated in a typical medical facility with access to electricity and clean water. The hemodialysis system may be powered by electricity provided by a conventional outlet. The hemodialysis system may also be configured to receive premade dialysate from a dialysate supply, such as a dialysate tank that provides dialysate to the dialysate circuit via a supply line. Thus, under normal operation, the hemodialysis system may not require a solar panel nor an atmospheric water generator.

An emergency or disaster situation may arise in proximity to the hemodialysis system that requires on-site dialysis treatments in environments that are not equipped to support such treatments. For example, it may not be possible to transport patients to the medical facility where the hemodialysis system resides for administering conventional dialysis treatments. Instead, the hemodialysis system may be transported to the disaster site, but the disaster site may not be equipped with the necessary resources.

In some examples, the hemodialysis system may be configured to operate in an alternative mode in which the hemodialysis system is powered by a solar panel (e.g., the solar panel 136 of FIG. 1). The hemodialysis machine may include an electrical interface (e.g., an electrical port) to which the solar panel can be connected. In some implementations, the hemodialysis system may include a battery (e.g., the battery 208 of FIG. 2) that is configured to store a charge that is derived from the electricity generated by the solar panel and/or electricity received via the electrical outlet. In this way, the hemodialysis machine can be unplugged from the electrical outlet and can instead be powered by electricity generated by the solar panel or provided by the battery at a location where electricity is otherwise unavailable.

In some examples, the hemodialysis machine is configured to be fitted with an atmospheric water generator (e.g., the atmospheric water generator 138 of FIG. 1) that is configured to extract water from ambient air on-site. The hemodialysis machine can also be fitted with a mixing chamber (e.g., the mixing chamber 140 of FIG. 1) that is configured to use the extracted water to generate dialysate. For example, the premade dialysate supply (e.g., the dialysate tank) may be removed from the hemodialysis machine and replaced with the atmospheric water generator and the mixing chamber. The atmospheric water generator may be connected to the mixing chamber such that the extracted water is provided to the mixing chamber. A concentrate such as a powdered sodium bicarbonate may be introduced into the mixing chamber. As water from the atmospheric water generator is added to the mixing chamber with the powdered sodium bicarbonate, a solution of sodium bicarbonate is created that can act as part of the dialysate. The mixing chamber can provide the dialysate to the dialysate circuit via the dialysate supply line.

Solid bicarbonate concentrate (e.g., powdered sodium bicarbonate) is typically more easily stored than sodium bicarbonate solution. Thus, the powdered sodium bicarbonate may be stored in sealed containers that allow for more prolonged storage. In this way, the dialysate can be generated on-site and on demand, thereby reducing the difficulties involved in storing dialysate.

In some implementations, the hemodialysis system can also include a forward osmosis container (e.g., the forward osmosis container 400 of FIG. 4). During normal operation, the hemodialysis system may be configured to provide premade saline from a saline bag to the patient via an IV line. However, in an alternative environment, the saline bag may instead be replaced with the forward osmosis container. In a manner similar to that described above with reference to FIG. 4, a salt concentrate may be placed in a first compartment of the forward osmosis container, and the water extracted by the atmospheric water generator can flow through a second compartment of the forward osmosis container. A semi-permeable membrane allows water to flow between the compartments and mix into a salt concentrate solution that has a salt concentration commensurate with saline. The salt concentrate solution can then be provided to the patient instead of the premade saline.

Like the solid bicarbonate concentrate used in the mixing chamber, the salt concentrate used in the forward osmosis container may be stored in sealed containers that allow for more prolonged storage. In this way, the saline can be generated on-site and on demand, thereby reducing the difficulties involved in storing saline under appropriate conditions.

After the disaster situation has subsided, the hemodialysis system may be returned to the medical facility and refitted with its base equipment. For example, the solar panel, the atmospheric water generator, the mixing chamber, and the forward osmosis container may be removed. The hemodialysis system may then reassume its principal operating mode in which the hemodialysis machine is powered by electricity provided by an electrical outlet and uses premade dialysate and saline during administration of dialysis treatments.

While certain implementations have been described, other implementations are possible.

While the solar panel has been described as including three solar modules, in some implementations, fewer or additional solar modules may be used. For example, in some implementations, the solar panel may include a single solar module that is pivotably attached to the dialysis machine. In some implementations, the solar panel may include any number of solar modules that can each be independently positioned.

While the solar panel has been described as being connected to a battery that stores a charge derived from the electricity generated by the solar panel, in some implementations, the electricity generated by the solar panel may power the dialysis machine directly (e.g., without the electricity first being stored by the battery). For example, the solar panel may be configured to generate an amount of electricity that is sufficient for on demand powering of the dialysis machine. In some implementations, the solar panel may be configured to deliver approximately 20 watts of power. In some implementations, the materials and dimensions of the solar panel can be chosen so as to allow the solar panel to generate and deliver any amount of power.

While the dialysis system has been described as including an atmospheric water generator, in some implementations, other water generators and/or water sources may be used. For example, the dialysis system may include a wet desiccant water generator. The wet desiccant water generator may include a salt (e.g., a salt in a concentrated brine solution) that is configured to absorb ambient humidity. Water can then be extracted from the brine solution and purified before being provided to components of the dialysis system.

While the water heater has been described as being incorporated into the storage container of the atmospheric water generator, in some implementations, the water heater is a separate component of the dialysis system. In some implementations, the atmospheric water generator provides the extracted water to the water heater as it is extracted from ambient air. The water heater may include a storage container where the heated water resides before it is provided to other portions of the dialysis machine.

While the dialysis system has been described as including a solar panel, an atmospheric water generator, a mixing chamber for generating dialysate, and a forward osmosis container for generating saline, in some implementations, one or more of these components may be omitted from the dialysis system.

In some implementations, the dialysis system may be located in an environment with access to a clean source of water, obviating the need for the atmospheric water generator. Thus, a different clean water source may provide water to the mixing chamber and/or the forward osmosis container for generating dialysate and/or saline.

In some implementations, the dialysis system may be located in an environment with access to dialysate and/or saline, obviating the need for the mixing chamber, the forward osmosis container, and/or the atmospheric water generator. Thus, the dialysate may be provided directly to the dialysate circuit via the dialysate supply line, and the saline may be provided directly to the patient via an IV line.

In some implementations, the dialysis system may be located in an environment with access to sufficient electricity for powering the dialysis system, obviating the need for the solar panel.

In some implementations, the dialysis system may include one or more of the solar panel, the atmospheric water generator, the mixing chamber for generating dialysate, and the forward osmosis container for generating saline even if such components are not readily necessary. For example, a dialysis system that is located in a medical facility may have access to electricity, a clean source of water, dialysate, and saline, yet the dialysis system may still include the solar panel, the atmospheric water generator, the mixing chamber, and the forward osmosis container to provide alternative ways to ensure uninterrupted operation of the dialysis system.

While the water extracted by the atmospheric water generator has been described as being used to generate dialysate and saline, in some implementations, the extracted water can also be used for other purposes. In some implementations, the extracted water can be mixed with calcium hypochlorite (e.g., bleach) to form a diluted bleach solution used for disinfecting components of the dialysis system.

In some of the above examples, the dialysis system has been described as having characteristics similar to those that exist in conventional dialysis systems. For example, the dialysis system has been described as being a dialysis system designed for operation in a traditional environment (e.g., a medical facility), but with the additional ability to be fitted with discrete components that allow the dialysis system to operate in alternative environments (e.g., disaster relief settings, underdeveloped regions, developing countries, etc.). However, in some implementations, the dialysis system can include one or more alternative or additional components that allow the dialysis system to operate in even more extreme environments (e.g., environments with little or no access to the sun, such as indoor disaster relief locations).

In some implementations, the dialysis system may include a generator configured to generate electricity in response to mechanical motions performed by an operator of the dialysis machine. The generator may include a mechanical component, such as a foot or hand powered crank, which generates electricity using electromagnetic induction during operation by an operator. The generator may be operated continuously or substantially continuously during a dialysis treatment to provide sufficient electricity for powering the dialysis machine. In some implementations, the dialysis system may also include a battery that is configured to store a charge derived from the electricity generated by the generator. The battery may be the same battery used to store the charge derived from the electricity generated by the solar panel, as described above. That is, the dialysis system may include both a solar panel and a generator that can be used alone or in concert to generate electricity.

While the blood pump (132 of FIG. 1) has been described as being controlled by a blood pump module 134 and the control unit 101, in some implementations, the dialysis system includes a blood pump that is manually controlled (e.g., by an operator of the dialysis machine). For example, the blood pump may include a mechanical component, such as a foot pump or a hand pump, which causes blood to pump to and from the patient during operation. In some implementations, the blood pump does not require control by the control unit or a blood pump module in order to operate. For example, the blood pump may include one or more valves (e.g., one-way valves) that are configured to control the flow rate of the blood pumped to and from the patient such that the flow rates are maintained within acceptable limits. The one-way valves can also prevent blood from flowing out of the patient, thereby preventing excessive blood loss in the patient. In this way, the operator can operate the foot pump or the hand pump at various rates without risk of harm to the patient.

In some implementations, the flow rate of the blood is controlled by one or more other components. For example, the blood flow rate may be controlled by other types of valves (e.g., other than one-way valves) that are configured to maintain the flow rate within acceptable limits. In some implementations, the dialysis system may include one or more sensors configured to measure the blood flow rate. For example, a flow sensor may be incorporated into blood lines of the blood circuit and/or the patient lines (e.g., the arterial and venous patient lines 106, 108 of FIG. 1). If the measured flow rate is unacceptable, the sensor may cause the flow rate to be adjusted (e.g., by adjusting a characteristic of a valve) or may cause the flow of blood to cease (e.g., by closing a valve). In some implementations, a sensor may be configured to detect a direction of flow of the blood. For example, if the sensor determines that blood is flowing in an unexpected direction, the sensor may provide a signal to the blood pump (132 of FIG. 1) that causes the blood pump to cease. In some implementations, a sensor may be configured to detect the presence of air in the blood lines. In some implementations, the sensor may cause an alert to be presented indicating that an error condition exists, such as an unacceptable blood flow rate, an unexpected flow direction of blood, and/or the presence of air in a blood line. The alert may be provided in the form of a message via the user interface (e.g., the touch screen 118), in the form of an audible alarm via a speaker, or in the form of a visual alarm via a flashing light, among others.

In some implementations, the blood pump may be configured to generate electricity in response to manual operation. For example, the mechanical component (e.g., the foot pump or the hand pump) may act as a generator in a manner similar to that described above with respect to the foot or hand powered cranks. The mechanical motion of the pump may generate electricity using electromagnetic induction. The generated electricity may be used to derive a charge that is stored in a battery of the dialysis system. In implementations in which the dialysis system includes a solar panel, the battery may be the same battery used for storing the charge derived from the electricity generated by the solar panel.

In some implementations, the dialysis system may be configured to operate in a low power mode. For example, in implementations in which the dialysis system is manually-powered by a generator, the generated electricity may be insufficient for completely operation of all features of the dialysis system. In such situations, the dialysis system may be configured to deactivate non-essential features in order to allow the generated electricity to sufficiently power essential features (e.g., features that are essential for patient safety).

While the dialysis system has been largely described as being a hemodialysis system, other medical treatment systems can employ the techniques described herein. Examples of other medical treatment systems include peritoneal (PD) dialysis systems, hemofiltration systems, hemodiafiltration systems, apheresis systems, and cardiopulmonary bypass systems.

In some implementations, the atmospheric water generator and the mixing chamber are used to generate a PD solution in a manner substantially similar to that described above with respect to generating dialysate. The PD solution can be provided to an abdominal cavity of a patient by a pump of the PD machine. The PD solution may be left to dwell for a period of time. During the dwelling period, toxins may be filtered from the patient's blood into the PD solution. The PD solution can then be drained from the patient.

Figure 5:
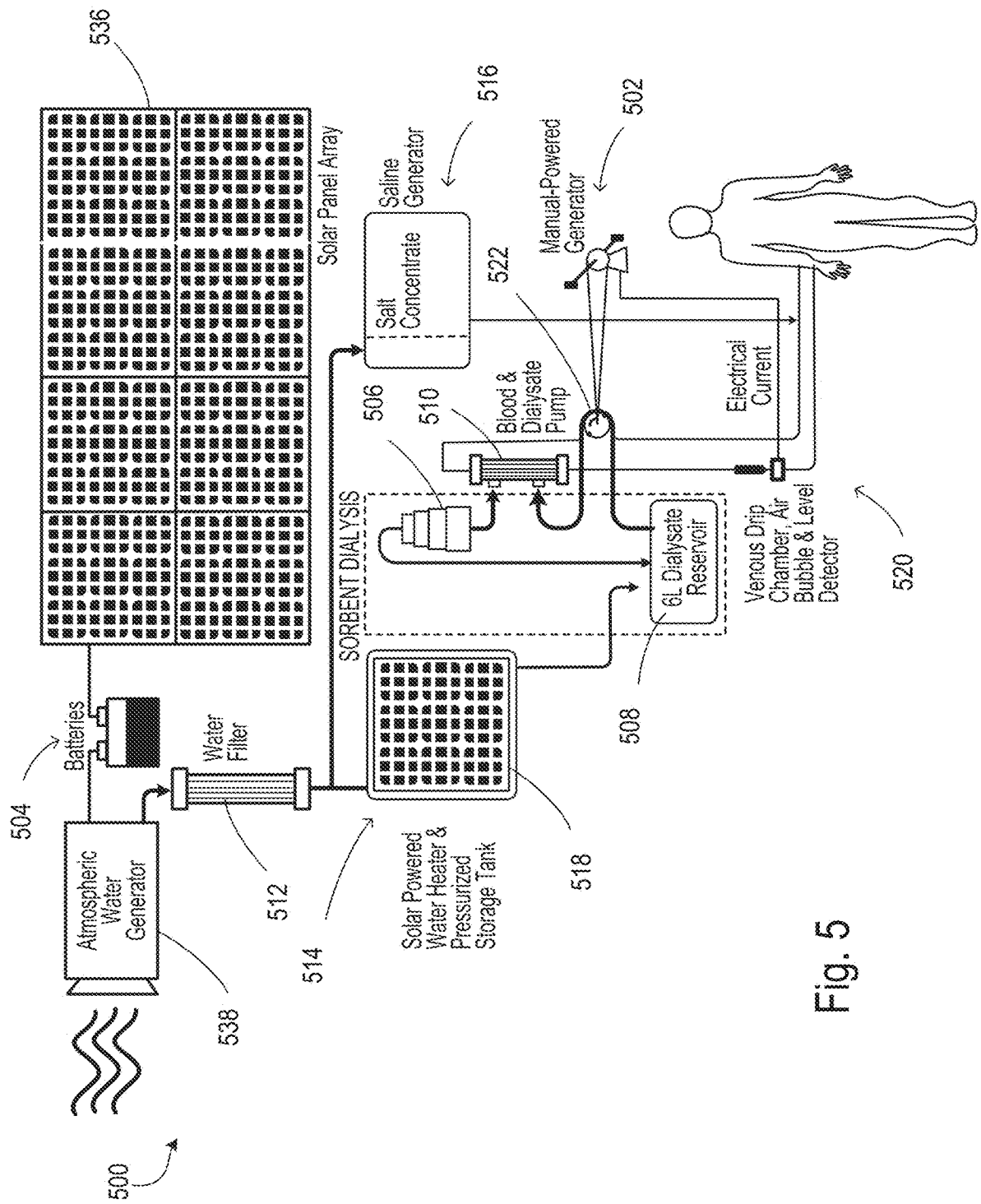
FIG. 5 shows a schematic view of a hemodialysis system that includes a manual-powered generator.

FIG. 5 shows a schematic view of a dialysis machine, such as a hemodialysis machine 500, configured for operating in an alternative environment. Although the dialysis machine described herein is largely discussed in connection with hemodialysis systems by way of example, it is explicitly noted that the dialysis machine described herein may be used in connection with other types of medical devices and treatments, including peritoneal dialysis (PD) systems. The hemodialysis machine 500 operates in a manner substantially similar to that described above with respect to the hemodialysis system 100 of FIG. 1, but with various modification as described in detail below.

The hemodialysis machine 500 includes a solar panel array 536 for generating electricity for powering components of the hemodialysis machine 500. The solar panel array 536 may include one or more electrically-connected solar modules, each of which may include one or more solar cells. The solar panel array 536 is configured to receive light energy in the form of photons and use the received light energy to generate electricity. The solar panel array 536 may include pivotable components that allow the solar panel array 536 to be oriented toward the sun.

The hemodialysis machine 500 also includes a manual-powered generator 502 that is configured to generate electricity in response to manual operation. The manual-powered generator 502 may include a mechanical component such as a foot crank or a hand crank that generates electricity using electromagnetic induction during operation by an operator. The manual-powered generator 502 may be operated continuously or substantially continuously during a dialysis treatment to provide sufficient electricity for powering the hemodialysis machine 500. The electricity used for powering the hemodialysis machine 500 may be generated by both the solar panel array 536 and the manual-powered generator 502 in any proportions. For example, the hemodialysis machine 500 may be powered in equal parts by the solar panel array 536 and the manual-powered generator 502. In some implementations, the hemodialysis machine 500 may be fully powered by the manual-powered generator 502 (e.g., when sunlight is not available). In some implementations, the hemodialysis machine 500 may be fully powered by the solar panel array 536 (e.g., when weather conditions permit such). In some implementations, the hemodialysis machine 500 may be partially powered by the solar panel array 536 and be supplemented with power from the manual-powered generator 502 to achieve a sufficient amount of electricity for proper operation of the hemodialysis machine 500.

The hemodialysis machine 500 includes one or more batteries 504 that are electrically connected to one or both of the solar panel array 536 and the manual-powered generator 502. The batteries 504 may be configured to store charge derived from the electricity generated by one or both of the solar panel array 536 and the manual-powered generator 502. In some implementations, a first battery is electrically connected to the solar panel array 536 and is configured to store the charge derived from the electricity generated by the solar panel array 536, and a second battery is electrically connected to the manual-powered generator 502 and is configured to store the charge derived from the electricity generated by the manual-powered generator 502. In some implementations, the hemodialysis machine 500 may be powered by the batteries 504 that store the charge derived from the electricity generated by the solar panel array 536 until the batteries 504 are depleted of charge, at which time the hemodialysis machine 500 may be powered on demand by the manual-powered generator 502 to allow for continued operation.

The hemodialysis machine 500 includes a pump 522 (e.g., a blood and dialysate pump) that is configured to circulate blood and dialysate through a blood circuit and a dialysate circuit of the dialysis machine 500. The hemodialysis machine 500 may also include a pump module (not shown) that the operator can interact with to operate the pump 522. In some implementations, the hemodialysis machine 500 includes separate pumps for pumping the blood and the dialysate through their respective circuits.

The dialysate circuit formed by a dialyzer 510, a sorbent device 506, and dialysate lines connecting the dialysate circuit to the hemodialysis machine 500. The dialysate circuit may also include additional dialysate components that reside inside a housing of the hemodialysis machine 500. During treatment, the pump 522 circulates blood through the blood circuit and dialysate through the dialysate circuit. A dialysate supply line carries fresh dialysate through the dialyzer 510, which serves as a filter for the patient's blood. The dialysate passes through the dialyzer 510 along with the blood. A semi-permeable structure (e.g., a semi-permeable membrane and/or semi-permeable microtubes) within the dialyzer 510 separates blood and dialysate passing through the dialyzer 510. This arrangement allows the dialysate to collect toxins from the patient's blood. The filtered blood exiting the dialyzer 510 is returned to the patient. The filtered blood may be returned to the patient via a venous drip chamber 520 that can include an air bubble and level detector. The dialysate exiting the dialyzer 510 (e.g., the spent dialysate) that includes the toxins removed from the blood is routed to the sorbent device 506.

The sorbent device 506 (e.g., the sorbent cartridge/filter) is configured to recycle spent dialysate so that the spent dialysate can be reused for further hemodialysis treatment. The sorbent device 506 may remove toxins (e.g., such as urea) from the spent dialysate, and the recycled dialysate can then be cycled back through the dialysate circuit for further cleansing of the patient's blood. Before being used for further cleansing, the recycled dialysate may be provided to a dialysate reservoir 508 that stores generated dialysate, as described in more detail below. The dialysate reservoir 508 may be configured to store approximately six liters of dialysate. The recycled dialysate may mix with generated dialysate, and the dialysate mixture may be cycled through the dialysate circuit for cleansing the patient's blood.

In some implementations, one or more desired substances (e.g., magnesium, calcium, potassium, sodium, etc.) may be stripped from the dialysate as the dialysate passes through the sorbent device 506. Such stripped substances can be added to the dialysate exiting the sorbent device 506 (e.g., prior to the dialysate being reintroduced into the dialysate circuit). In some implementations, water can be introduced into the recycled dialysate for dilution purposes if the sodium concentration of the recycled dialysate is too high.

The hemodialysis machine 500 includes an atmospheric water generator 538 that is configured to extract water from humidity in ambient air and provide the extracted water to one or more portions of the hemodialysis machine 500. The atmospheric water generator 538 may operate in a manner substantially similar to that described above with respect to the atmospheric water generator 138 of FIGS. 1 and 3. The extracted water is provided to a water filter 512 (e.g., an ultrapure filter) that removed unwanted substances from the extracted water. The extracted water is then provided to a water storage tank 514 and a forward osmosis container 516.

The water storage tank 514 includes a water heater for heating the extracted water before it is used to generate dialysate. The water heater may include one or more heating elements that are configured to heat, pressurize, and/or degas the extracted water so as to produce ISO quality water. In some implementations, the water heater is solar powered. For example, the water heater may include a solar panel array 518 (e.g., separate from the solar panel array 536 described above) that is configured to generate electricity that is used to power the heating elements. In some implementations, the water heater is powered by electricity generated by one of both of the solar panel array 536 and the manual-powered generator 502. In some implementations, the water heater is electrically connected to and powered by the batteries 504.

The water storage tank 514 provides the extracted water to the dialysate reservoir 508. In some implementations, the extracted water is provided to a mixing chamber (not shown) before it is provided to the dialysate reservoir 508. The mixing chamber may operate in a manner substantially similar to that described above with respect to the mixing chamber 140 of FIG. 1. In particular, the extracted water may mix with a concentrate (e.g., a solid concentrate), such as a powdered sodium bicarbonate, to produce a mixed sodium bicarbonate solution that is used as the dialysate. The mixing chamber may then provide the dialysate to the dialysate reservoir 508. In some implementations, the dialysate reservoir 508 itself may act as the mixing chamber. That is, the dialysate reservoir 508 may include a concentrate that mixes with the extracted water to generate the dialysate that is circulated through the dialysate circuit.

In some implementations, the hemodialysis machine 500 does not include a separate mixing chamber for producing dialysate. Instead, the sorbent device 506 may be used to generate the dialysate. For example, the extracted water may be provided to the dialysate reservoir 508 where it is initially circulated (e.g., by the pump 522) through the dialysate circuit to the sorbent device 506. The sorbent device 306 may include one or more substances that mix with the extracted water to generate dialysate. The generated dialysate is then stored in the dialysate reservoir 508 for use in a dialysis treatment. The dialysate may then be circulated through the dialyzer 510 along with the patient's blood in order to remove toxins from the blood. The spent dialysate may then be provided to the sorbent device 506 to be recycled for further use. The recycled dialysate may be provided to the dialysate reservoir 508.

The extracted water is also provided to the forward osmosis container 516 where it is used to generate saline. The forward osmosis container 516 may operate in a manner substantially similar to that described above with respect to the forward osmosis container 400 of FIG. 4. The forward osmosis container 516 may be in the form of a bag (e.g., a disposable bag). The forward osmosis container 516 includes a first compartment, a second compartment, and a semi-permeable membrane therebetween. In some implementations, the semi-permeable membrane is disposable.

A salt concentrate such as sodium chloride may be stored in the first compartment, and the extracted water may enter the second compartment. As the water is introduced, the semi-permeable membrane allows the water to pass into the first compartment with the salt concentrate without allowing the salt concentrate to pass into the second compartment with the water. The mixing of the water and the salt concentrate results in a high-concentration salt concentrate solution accumulating in the first compartment. As water continues to be introduced into the second compartment, a relatively lower-concentration salt concentrate solution accumulates in the second compartment. The lower-concentration salt concentration solution may have a salt concentration commensurate with saline that can be provided to the patient.

While the hemodialysis machine 500 is shown as including a manual-powered generator 502 and a separate pump 522, in some implementations, the manual-powered generator 502 may itself act as a pump for pumping one or both of blood and dialysate through the hemodialysis machine 500. For example, the hemodialysis machine 500 may include one or more manual pumps that include a mechanical component, such as a foot pump or a hand pump, which causes blood and/or dialysate to pump through their respective circuits of the hemodialysis machine 500. In some implementations, the manual pump does not require control by a control unit or a pump module in order to operate. For example, the manual pump may include one or more valves (e.g., one-way valves) that are configured to control the flow rate of blood and/or dialysate. The valves may be configured to maintain the flow rate of blood to and from the patient within acceptable limits. The valves may also prevent blood from flowing out of the patient, thereby preventing excessive blood loss in the patient. In this way, the operator can operate the foot pump or the hand pump at various rates without risk of harm to the patient. The mechanical component may also be configured to generate electricity, as described above with respect to the manual-powered generator 502. For example, the mechanical component (e.g., the foot pump or the hand pump) may act as a generator in a manner similar to that described above with respect to the foot or hand powered cranks.

Figure 6:
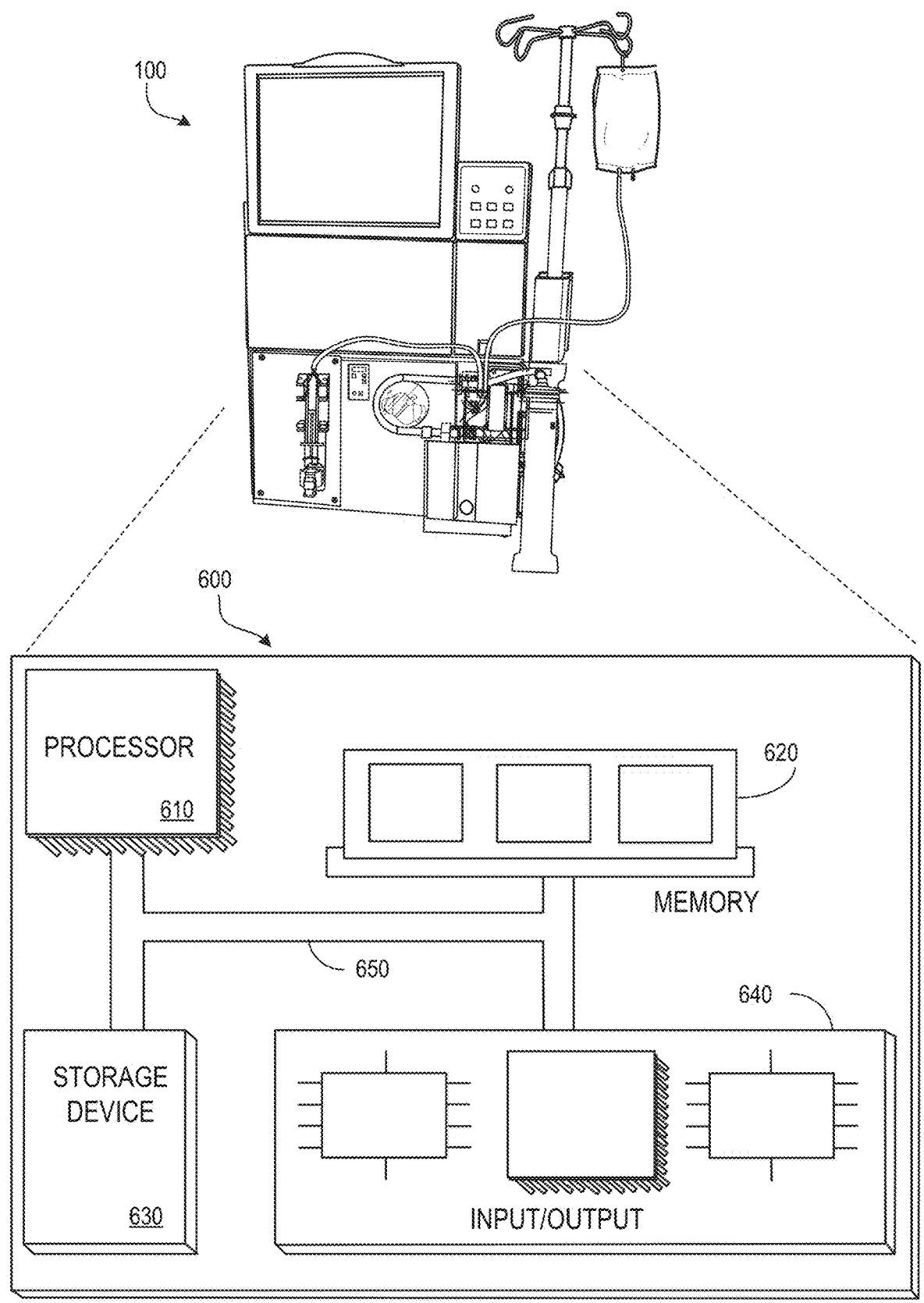
FIG. 6 is a block diagram of an example computer system.

FIG. 6 is a block diagram of an example computer system 600. For example, referring to FIG. 1, the control unit 101 could be an example of the system 600 described here. The system 600 includes a processor 610, a memory 620, a storage device 630, and an input/output device 640. Each of the components 610, 620, 630, and 640 can be interconnected, for example, using a system bus 650. The processor 610 is capable of processing instructions for execution within the system 600. The processor 610 can be a single-threaded processor, a multi-threaded processor, or a quantum computer. The processor 610 is capable of processing instructions stored in the memory 620 or on the storage device 630. The processor 610 may execute operations such as causing the dialysis system to carry out functions related to voice commands, voice alarms, and voice instructions.

The memory 620 stores information within the system 600. In some implementations, the memory 620 is a computer-readable medium. The memory 620 can, for example, be a volatile memory unit or a non-volatile memory unit. In some implementations, the memory 620 stores information related to patients' identities.

The storage device 630 is capable of providing mass storage for the system 600. In some implementations, the storage device 630 is a non-transitory computer-readable medium. The storage device 630 can include, for example, a hard disk device, an optical disk device, a solid-date drive, a flash drive, magnetic tape, or some other large capacity storage device. The storage device 630 may alternatively be a cloud storage device, e.g., a logical storage device including multiple physical storage devices distributed on a network and accessed using a network. In some implementations, the information stored on the memory 620 can also or instead be stored on the storage device 630.

The input/output device 640 provides input/output operations for the system 600. In some implementations, the input/output device 640 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 640 includes driver devices configured to receive input data and send output data to other input/output devices, e.g., a keyboard, a printer, and display devices (such as the touch screen display 118). In some implementations, mobile computing devices, mobile communication devices, and other devices are used.

In some implementations, the system 600 is a microcontroller. A microcontroller is a device that contains multiple elements of a computer system in a single electronics package. For example, the single electronics package could contain the processor 610, the memory 620, the storage device 630, and input/output devices 640.

Although an example processing system has been described in FIG. 6, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations of the invention have been described. Nevertheless, it will be understood that various modifications may be made without departing from the spirit and scope of the invention. Accordingly, other implementations are within the scope of the following claims.

What is claimed is:

1. A hemodialysis machine operable in multiple modes, the hemodialysis machine comprising:
    a blood pump configured to pump blood to and from a patient;
    an electrical interface;
    a removable solar panel module configured to connect to the electrical interface and receive light energy and generate electricity;
    a removable atmospheric water generator configured to be powered by the generated electricity and configured to extract water from ambient air and pump a first portion of the extracted water to a removable mixing chamber;
    the mixing chamber configured to mix one or more substances with the first portion of the extracted water to generate dialysate; and
    a dialyzer configured to receive the blood and the dialysate, remove toxins from the blood, and provide filtered blood to the patient, wherein, in a first configuration, the hemodialysis machine operates in an emergency mode using the solar panel module, the atmospheric water generator and the mixing chamber, and wherein, in a second configuration, the hemodialysis machine operates in a clinic mode in which the solar panel module, the atmospheric water generator and the mixing chamber are removed and in which the electrical interface is connected to a power outlet and the dialyzer receives the dialysate from a dialysate supply line.

2. The hemodialysis machine of claim 1, comprising a battery configured to store a charge derived from the generated electricity.

3. The hemodialysis machine of claim 1, comprising a water heater configured to heat the extracted water.

4. The hemodialysis machine of claim 3, wherein the water heater comprises a container for storing heated water.

5. The hemodialysis machine of claim 3, wherein the water heater comprises a second solar panel module configured to receive light energy that is used to heat the extracted water.

6. The hemodialysis machine of claim 1, wherein the blood pump comprises a mechanical component that is configured to be manually operated.

7. The hemodialysis machine of claim 6, wherein the mechanical component comprises one or both of a hand pump and a foot pump.

8. The hemodialysis machine of claim 6, wherein the mechanical component is configured to generate electricity in response to manual operation of the blood pump.

9. The hemodialysis machine of claim 8, comprising a battery configured to store a charge derived from the electricity generated by one or both of the mechanical component and the solar panel.

10. The hemodialysis machine of claim 1, wherein the blood pump comprises one or more valves configured to control a flow rate of the blood pumped to and from the patient.

11. The hemodialysis machine of claim 1, comprising a forward osmosis container configured to produce a salt concentrate solution from a second portion of the extracted water, the forward osmosis container comprising:
    a first compartment configured to store a salt concentrate;
    a second compartment configured to receive the second portion of the extracted water; and
    a membrane that separates the first compartment from the second compartment, the membrane configured to allow the second portion of the extracted water to mix with the salt concentrate to produce the salt concentrate solution.

12. The hemodialysis machine of claim 11, wherein the forward osmosis container further comprises one or more conductivity sensors configured to ensure that the salt concentration solution has a salt concentration commensurate with saline solution.

13. The hemodialysis machine of claim 1, further comprising a sorbent device configured to (i) remove toxins from spent dialysate flowing from the dialyzer to produce recycled dialysate, and (ii) provide the recycled dialysate to the dialyzer for further cleansing of the patient's blood.

* * * * *